United States Patent [19]

Yeh et al.

[11] Patent Number: 4,612,191
[45] Date of Patent: Sep. 16, 1986

[54] STAIN REMOVAL TOOTHPASTE

[75] Inventors: Kuo-Chen Yeh, Westfield; Joseph Synodis, New Providence, both of N.J.

[73] Assignee: Block Drug Co., Inc., Jersey City, N.J.

[21] Appl. No.: 643,405

[22] Filed: Aug. 23, 1984

[51] Int. Cl.$^4$ .......................... A61K 7/16; A61K 7/18
[52] U.S. Cl. .......................................... 424/52; 424/49
[58] Field of Search ...................................... 424/49–58

[56] References Cited

U.S. PATENT DOCUMENTS

| | | | |
|---|---|---|---|
| 2,820,000 | 1/1958 | Menzies | 424/49 |
| 3,946,108 | 3/1976 | Tomlinson et al. | 424/49 |
| 4,108,978 | 8/1978 | Mazzanobile et al. | 424/49 |
| 4,108,979 | 8/1978 | Muhler et al. | 424/52 |
| 4,109,981 | 8/1978 | Muhler et al. | 424/52 |
| 4,122,163 | 10/1978 | Muhler et al. | 424/52 |
| 4,414,199 | 11/1983 | Strobridge | 424/52 |
| 4,428,928 | 1/1984 | Muhler et al. | 424/52 |

FOREIGN PATENT DOCUMENTS 1552119  9/1979  United Kingdom ............... 424/56

*Primary Examiner*—Shep K. Rose
*Attorney, Agent, or Firm*—Ostrolenk, Faber, Gerb & Soffen

[57] ABSTRACT

A toothpaste having high polishing and cleaning properties suitable for use in the removal of coffee and tea stains comprises about 10-35% of an abrasive system combined with a non-toxic paste, said abrasive system comprising a combination of anhydrous aluminum silicate and diatomaceous silica in a ratio of about 0.5:1–1.5:1, said toothpaste having a radioactive dentin abrasion index not in excess of about 150. The system provides excellent fluoride stability during storage and does not interfere with fluoride bioavailability.

14 Claims, No Drawings

STAIN REMOVAL TOOTHPASTE

BACKGROUND OF THE INVENTION

In order to be effective in cleaning the teeth, dentifrices must contain a polishing agent or an abrasive ingredient such as calcium carbonate, dicalcium phosphate, tricalcium phosphate, calcium pyrophosphate, sodium metaphosphate, hydrate silica and the like. Some stains, particularly coffee and tea stains, tenaciously adhere to the tooth surfaces and are, therefore, much more difficult to remove. While a more abrasive polishing agent can be used, those generally result in damage to the oral hard tissues after prolonged use of the dentifrice.

It has now been found that a dentifrice containing an appropriate amount of a particular abrasive system, namely a combination of anhydrous aluminum silicate and diatomaceous earth (silica), can be used to provide a high polishing, high cleaning dentifrice which is not overly abrasive (radioactive dentin abrasion index in the 130-150 range). Other abrasive agents can also be present, if desired.

Dentifrices containing diatomaceous silica are known. Thus, U.S. Pat. No. 2,820,000 describes a dentifrice containing primarily diatomaceous earth (silica). However, this abrasive alone does not provide a high polishing and high cleaning formulation which is not overly abrasive.

U.S. Pat. Nos. 3,906,090 and 4,364,579 teach dentifrices containing interbonded silicates and alumina, for example sodium aluminosilicate complex, as abrasives. These interbonded silicates and alumina are chemically different from the anhydrous aluminum silicate and diatomaceous earth (silica) of the present invention and none of the silicates or alumina, being mildly abrasive, are very effective cleaning agents. The combination of the anhydrous aluminum silicate with diatomaceous earth (silica) provides a high polishing and cleansing dentifrice with superior cleaning capabilities to that provided by using either of these polishing agents alone. The combination also provides superior cleaning efficacy compared to the leading commercial family toothpaste (which contains a milder abrasive system) but the combination is not so abrasive so as to damage the oral tissues. The combination also provides superior cleaning efficacy compared to a commercial dentifrice which is specifically promoted for removal of tobacco stains.

It is accordingly the object of this invention to provide a new dentifrice which has high polishing and cleaning properties suitable for removal of tenacious stains on teeth, such as coffee and tea stains, yet not be too abrasive so as to damage the oral tissues with daily use. This and other objects of the invention will become apparent to those skilled in the art from the following detailed description.

SUMMARY OF THE INVENTION

This invention relates to a toothpaste having high polishing and cleaning properties suitable for the removal of coffee and tea stains without being too abrasive. More particularly, the toothpaste comprises an abrasive system in a non-toxic paste, the abrasive system comprising a combination of anhydrous aluminum silicate and diatomaceous earth (silica) in a ratio of about 0.5:1-1.5:1, the toothpaste having a radioactive dentin abrasion index which does not exceed about 150.

DESCRIPTION OF THE INVENTION

A toothpaste having high polishing and cleaning properties suitable for the removal of tenacious coffee and tea stains contains an abrasive system in a non-toxic paste. The abrasive system contains, as an essential ingredient, a combination of anhydrous aluminum silicate and diatomaceous earth (silica).

The anhydrous aluminum silicate should optimally have an average particle size of less than about 1 micron to provide high polishing properties without undue abrasivity; however, slightly larger average particle sizes (up to about 1.5 microns) would be suitable for this application. The whiteness of the anhydrous aluminum silicate selected for use may be an important attribute as well since commercially available U.S.P. Kaolin (anhydrous aluminum silicate) has an off-white tint which may impart unwanted color or shading to finished product.

The diatomaceous earth (silica) should optimally have a median particle size of about 5.5 microns with about 25% or less of the particles having particle sizes greater than about 8 microns. Both of these essential ingredients are commercially available. For example, the anhydrous aluminum silicate is available under the trademark Kaopolite SF and the diatomaceous earth (silica) is available under the trademark Superfloss. The anhydrous aluminum silicate generally is about 5–15% of the dentifrice, preferably about 8–12% and the diatomaceous earth (silica) is generally about 5–20%, preferably about 12–18% of the dentifrice. The ratio of silicate to silica is about 0.5:1–1.5:1.

The abrasive system in the dentifrice can contain other abrasive agents if desired. Such other abrasives include calcium carbonate, dicalcium phosphate, tricalcium phosphate, calcium pyrophosphate, the corresponding water insoluble magnesium salts, hydrated silica, alumina trihydrate, and the like. Such other abrasives are not essential and, indeed, it has been found that a combination of 10% anhydrous aluminum silicate and 15% diatomaceous silica based on the weight of the dentifrice, i.e. a ratio of about 0.67:1, provides an excellent high polishing, high cleaning dentifrice which is not overly abrasive.

The abrasive system will generally be about 10–35% of the dentifrice. The most preferred present formula contains about 25% of the abrasive system. In general, raising the level of the abrasive system does not significantly improve the cleaning capacities of the dentifrice but it can significantly increase the radioactive dentin abrasion index and thus result in potential damage to the oral hard tissues. This is demonstrated in the examples below. The radioactive dentin abrasion index of the dentifrice should not exceed about 150 and preferably the average index should not exceed about 130.

The balance of the dentifrice is a conventional non-toxic paste. Any conventional paste composition can be used. As such, paste vehicles provide a mass of a consistency which desirably can be extruded from a container such as an aluminum tube, a glaminated tube or a pump type dispenser. In general, the paste contains water usually combined with a humectant such as glycerine, sorbitol or the like.

The paste often contains organic surface active agents which can be anionic, nonionic, ampholytic or cationic in nature. It is preferred to employ as the surfactant a material which inparts detersive and foaming properties to the composition. Examples of detergents which can be used include the water soluble salts of higher fatty acid monoglyceride monosulfates such as monosulfated monoglyceride of hydrogenated coconut oil fatty acids sodium salt, higher alkyl sulfates such as sodium lauryl sulfate, alkyl aryl sulfonates such as sodium dodecyl sulfonate, olefin sulfonates such as sodium olefin sulfonate in which the olefin group contains 12-21 carbon atoms, higher alkyl sulfoacetates, higher fatty acid esters of dihydroxy propane sulfonates, substantially saturated higher aliphatic acylamides of lower aliphatic amino carboxylic acid compounds, condensates of ethylene oxide with sorbitan monostearate or with propylene oxide condensates of propylene glycol, guaternized imidazole derivatives and the like.

Any suitable flavoring or sweetening material can be employed. Examples include the flavoring oils such as the oils of spearmint, peppermint, wintergreen, clove, eucalyptus, as well as methylsalicylate. Suitable sweetening agents include sorbitol, sodium cyclamate, sodium saccharin, aspartame and the like.

The dentifrice can also contain a suitably selected fluoride containing compound having a beneficial effect on the care and hygiene of the oral cavity. Examples of known fluoride compounds in this category include sodium fluoride, stannous fluoride, potassium fluoride, potassium stannous fluoride, sodium hexafluorostanate, stannous chlorofluoride, sodium fluorozirconate, and sodium monofluorophosphate. Sodium fluoride and sodium monofluorophosphate are particularly preferred. The dentifrice abrasive combination provides for excellent fluoride stability during product aging and does not interfere with fluoride bioavailability as measured by enamel fluoride uptake and enamel reduction studies.

The dentifrice can also contain coloring or whitening agents or dyestuffs, preservatives, and the like. If desired, a gelling agent such as the natural and synthetic gums and gum-like materials exemplified by gum tragacanth, hydroxyethylcellulose, carboxymethylcellulose, polyvinyl pyrrolidone and the like, can be used. The various ingredients of the dentifrice are compounded in the conventional fashion.

In order to further illustrate the invention, the various examples are set forth below. In these examples, as well as throughout this specification and claims, all parts and percentages are by weight.

EXAMPLE 1

A dentifrice was prepared from the following ingredients:

| Ingredient | Function | Percentage |
| --- | --- | --- |
| Sodium monofluorophosphate | Anti-caries | 0.8% |
| Sodium saccharin | Sweetener | 0.2% |
| Titanium dioxide | Opacifier | 2.0% |
| Anhydrous aluminum silicate | Abrasive | 10% |
| Diatomaceous earth (silica) | Abrasive | 15% |
| Glycerin | Humectant | 10% |
| Sorbitol | Humectant | 10% |
| Hydroxyethyl cellulose | Binder (gelling agent) | 2.0% |
| Sodium lauryl sulphate | Detergent | 1.5% |
| Flavor mix | Flavor | 1.2% |
| Water | Vehicle | q.s. to 100% |

EXAMPLE 2

A dentifrice was prepared from the following ingredients:

| Ingredient | Function | Percentage |
| --- | --- | --- |
| Sodium monofluorophosphate | Anti-caries | 0.8% |
| Sodium saccharin | Sweetener | 0.2% |
| Titanium dioxide | Opacifier | 1.0% |
| Dicalcium phosphate anhydrous | Abrasive | 8% |
| Anhydrous aluminum silicate | Abrasive | 8% |
| Diatomaceous silica | Abrasive | 10% |
| Glycerin | Humectant | 10% |
| Sorbitol | Humectant | 15% |
| Hydroxyethyl cellulose | Binder (gelling agent) | 1.2% |
| Sodium lauryl sulphate | Detergent | 1.5% |
| Flavor mix | Flavor | 1.3% |
| Water | Vehicle | q.s. to 100% |

EXAMPLE 3

Comparative Composition

A dentifrice was prepared from the following ingredients:

| Ingredient | Function | Percentage |
| --- | --- | --- |
| Sodium monofluorophosphate | Anti-caries | 0.8% |
| Sodium saccharin | Sweetener | 0.2% |
| Titanium dioxide | Opacifier | 1.5% |
| Dicalcium phosphate anhydrous | Abrasive | 15% |
| Anhydrous aluminum silicate | Abrasive | 8% |
| Diatomaceous earth (silica) | Abrasive | 15% |
| Glycerin | Humectant | 10% |
| Sorbitol | Humectant | 10% |
| Hydroxyethyl cellulose | Binder (gelling agent) | 1.0% |
| Sodium lauryl sulphate | Detergent | 1.0% |
| Flavor mix | Flavor | 1.0% |
| Water | Vehicle | q.s. to 100% |

EXAMPLE 4

Cleaning Efficacy

A cleaning study was carried out using an in vitro coffee-tea stained pellicle model developed at the Oral Health Research Institute, Indiana University, and described in J. Dent. Res. 61(11): 1236-1239, 1982. In this study, the dentifrices of Examples 1, 2, and 3 were compared to a leading commercial family toothpaste, Crest, which contains hydrate silica as the abrasive and to a leading commercial stain removal toothpaste, Topol/F, which uses insoluble sodium metaphosphate as the abrasive. The results obtained were as follows:

| Dentifrice | Cleaning Ratio | Radioactive Dentin Abrasion Index |
| --- | --- | --- |
| Example 1 | 132 | 129 ± 20 |
| Example 2 | 121 | 121 ± 18 |
| Example 3 | 127 | 174 ± 15 |
| Crest | 100 | 106 ± 14 |
| Topol/F | 90 | 103 ± 4 |

The results set forth in the foregoing table demonstrate that the dentifrices of Examples 1, 2 and 3 provide superior cleaning efficacy compared to the leading commercial family toothpaste Crest and a leading stain removal toothpaste Topol/F. The Table also shows that the Example 3 dentifrice, while providing a superior cleaning efficacy to Crest and Topol/F, was too abrasive as shown by the radioactive dentin abrasion index of 174, which may lead to damage of oral tissues. Examples 1 and 2 provide a similar superior cleaning performance (see cleaning ratios with Crest defined as 100) while maintaining an acceptacle abrasivity level.

Various changes and modifications can be made in the dentifrice of the present invention without departing from the spirit and scope thereof. The various embodiments which were described herein were for the purpose of further illustrating the invention but were not intended to limit it.

What is claimed is:

1. A dentifrice having high polishing and cleaning properties suitable for removal of coffee and tea stains comprising about 10–35% of an abrasive system in combination with a non-toxic paste, said abrasive system comprising a combination of about 5–15% anhydrous aluminum silicate and about 5–20% diatomaceous silica in a ratio of about 0.5:1 to about 1.5:1, said dentifrice having a radioactive dentin abrasion index not in excess of about 150.

2. The dentifrice of claim 1 having a radioactive dentin abrasion index of about 100–150.

3. The dentifrice of claim 2 in which the abrasive system comprises a combination of about 8–12% anhydrous aluminum silicate and about 12–18% diatomaceous silica in a ratio of about 0.67:1.

4. The dentifrice of claim 3 in which the abrasive system is about 25% thereof.

5. The dentifrice of claim 4 having an average radioactive dentin abrasion index of about 130.

6. The dentifrice of claim 4 wherein said non-toxic paste comprises water, humectant, binder, detergent and flavoring agent.

7. The dentifrice of claim 6 in which the non-toxic paste contains a fluoride-providing compound.

8. The dentifrice of claim 6 in which the fluoride-providing compound is sodium monofluorophosphate.

9. The dentifrice of claim 5 wherein said non-toxic paste comprises water, humectant, binder, detergent and flavoring agent.

10. The dentifrice of claim 9 in which the non-toxic paste contains a fluoride-providing compound.

11. The dentifrice of claim 10 in which the fluoride-providing compound is sodium monofluorophosphate.

12. The dentifrice of claim 1 in which the non-toxic paste contains a fluoride-providing compound.

13. The dentifrice of claim 12 in which the fluoride-providing compound is sodium monofluorophosphate.

14. The dentifrice of claim 12 in which the fluoride-providing compound is sodium fluoride.

* * * * *